United States Patent
Brisebois

(10) Patent No.: US 6,465,711 B1
(45) Date of Patent: Oct. 15, 2002

(54) ABSORBENT ARTICLE HAVING AN IMPROVED COVER LAYER

(75) Inventor: Henri Brisebois, Lachenaie (CA)

(73) Assignee: Johnson & Johnson Inc., Montreal (CA)

(*) Notice: Subject to any disclaimer, the term of this patent is extended or adjusted under 35 U.S.C. 154(b) by 0 days.

(21) Appl. No.: 09/569,685

(22) Filed: May 12, 2000

(51) Int. Cl.[7] .................................................. A61F 13/46
(52) U.S. Cl. ................................ 604/378; 604/385.101
(58) Field of Search .......................... 604/378, 385.101, 604/385.04, 383, 385.01, 385.08

(56) References Cited

U.S. PATENT DOCUMENTS

| | | | |
|---|---|---|---|
| 3,559,648 A | * | 2/1971 | Mason, Jr. .................. 128/287 |
| 4,077,410 A | | 3/1978 | Butterworth et al. |
| 4,216,772 A | | 8/1980 | Tsuchiya et al. |
| 4,307,721 A | | 12/1981 | Tsuchiya et al. |
| 4,377,615 A | | 3/1983 | Suzuki et al. |
| 4,468,428 A | | 8/1984 | Early et al. |
| 4,537,822 A | | 8/1985 | Nanri et al. |
| 4,555,430 A | | 11/1985 | Mays |
| 4,690,679 A | | 9/1987 | Mattingly et al. |
| 4,728,394 A | | 3/1988 | Shinjou et al. |
| 4,762,521 A | * | 8/1988 | Roessler et al. ........ 604/38 SA |
| 4,801,494 A | | 1/1989 | Datta et al. |
| 4,810,556 A | | 3/1989 | Kobayashi et al. |
| 4,868,031 A | | 9/1989 | Modrak et al. |
| 4,892,534 A | | 1/1990 | Datta et al. |
| 5,047,023 A | * | 9/1991 | Berg .......................... 604/368 |
| 5,133,835 A | | 7/1992 | Goettmann et al. |
| 5,171,238 A | | 12/1992 | Kajander |
| 5,188,624 A | * | 2/1993 | Young, Sr. et al. ......... 604/378 |
| 5,204,165 A | | 4/1993 | Schortmann |
| 5,257,982 A | | 11/1993 | Cohen et al. |
| 5,271,780 A | | 12/1993 | Baigas, Jr. |
| 5,281,208 A | * | 1/1994 | Thompson et al. ......... 604/378 |
| 5,403,444 A | | 4/1995 | Goettmann et al. |
| 5,423,788 A | * | 6/1995 | Rollins et al. ........... 604/385.1 |
| 5,437,653 A | | 8/1995 | Gilman et al. |
| 5,486,166 A | | 1/1996 | Bishop et al. |
| 5,490,846 A | | 2/1996 | Ellis et al. |
| 5,514,120 A | * | 5/1996 | Johnston et al. ............ 604/378 |
| 5,649,916 A | * | 7/1997 | DiPalma et al. ............ 604/378 |
| 5,961,505 A | * | 10/1999 | Coe et al. .................. 604/378 |
| 5,998,696 A | * | 12/1999 | Schone ...................... 604/378 |
| 6,013,063 A | * | 1/2000 | Roe et al. ................ 604/385.1 |
| 6,022,338 A | * | 2/2000 | Putzer ..................... 604/385.1 |
| 6,117,523 A | * | 9/2000 | Sugahara .................... 428/134 |
| 6,262,331 B1 | * | 7/2001 | Nakahata et al. ........... 604/383 |
| 6,319,239 B1 | * | 11/2001 | Daniels et al. ......... 604/385.01 |
| 6,222,092 B1 | * | 4/2002 | Hansen et al. ............. 604/378 |
| 2001/0029359 A1 | * | 10/2001 | Carlucci ................ 604/385.12 |

FOREIGN PATENT DOCUMENTS

WO    WO93/09744 A1    5/1993

* cited by examiner

Primary Examiner—Aaron J. Lewis
Assistant Examiner—Michael Bogart
(74) Attorney, Agent, or Firm—James P. Barr

(57) ABSTRACT

A sanitary absorbent article such as a sanitary napkin, pantiliner or incontinence pad having a cover layer featuring an intermediate zone and two terminal zones. The intermediate zone has two marginal portions adjacent the longitudinal sides of the sanitary napkin. At least the marginal portions and preferably the entire intermediate zone are formed of material that has a higher degree of vertical liquid migration than lateral liquid migration. The terminal zones are made of material that has a higher degree of lateral liquid migration than vertical liquid migration.

20 Claims, 5 Drawing Sheets

ABSORBENT ARTICLE HAVING AN IMPROVED COVER LAYER

FIELD OF THE INVENTION

The present invention relates to sanitary absorbent articles such as sanitary napkins, pantiliners and adult incontinence pads. More specifically, it relates to the construction of the body faceable cover layer of such articles.

BACKGROUND OF THE INVENTION

Sanitary absorbent articles are articles of manufacture that generally are used to absorb and retain bodily exudates; they have both medical and non-medical uses. Conventional sanitary absorbent articles generally comprise several different layers of material joined together to form a laminate. Each of these layers is referred to as a "component layer" and serves a specific function within the article. Each layer is thus usually fabricated from a material different than that of the others, and has different physical properties and characteristics.

The uppermost layer of material, i.e. the layer that is intended to face the body of a wearer of the article when the article is in use is conventionally termed the "cover layer" or "top sheet". The cover layer is generally relatively soft to the touch so as to avoid discomfort and prevent abrasions to the human tissue with which it is in contact during the time which the article is worn. The cover layer is fluid permeable to permit the ingress of bodily exudate into the article to be absorbed and retained. At the same time, however, the cover layer preferably remains dry to prevent moisture from accumulating against the skin of the wearer causing irritation. In order to meet these desired characteristics, conventional cover layers are manufactured from non-woven fibrous materials or polymeric, preferably thermoplastic, films, having a large number of relatively small apertures per unit surface area. Each of these types of materials is well known in the art.

Neither of these materials is, however, without its drawbacks. Non-woven fibrous materials have the characteristic of planar (lateral) wicking. As described above, it is generally desired that bodily exudate to be absorbed by the article pass through the cover layer to the absorbent layer therebelow. As non-woven cover layers comprise fibrous components, however, some bodily exudate will wick in the plane of a cover layer owing to the capillary action of the fibers thereof. Depending on the quantity of exudate impinging upon the cover layer, such bodily exudate will eventually migrate to the sides of the article and will egress the cover layer and soil the garments (or undergarments) of the wearer. In many non-woven cover materials the fibers are generally oriented all in the same direction, usually either parallel to the longitudinal centerline or to the transverse centerline of the article (these axes are well known to those skilled in art and are also defined below). In these covers the majority of lateral wicking occurs in a direction parallel to that of the fiber direction. As the length of the article in a direction parallel to the transverse centerline is shorter than that in a direction parallel to the longitudinal centerline, this problem is therefore much worse when the fibers are oriented parallel to the transverse centerline, particularly in a central region of the article.

In contrast, apertured thermoplastic films do not generally wick fluids within the plane of the film, as they do not comprise fibrous elements, nor are they intrinsically absorbent. Thus, substantially no lateral wicking occurs and substantially the entirety of exudate impinging upon cover layers of these materials passes therethrough to the absorbent layer below. The disadvantage of such materials is that they may feel hot and sticky against the skin of a wearer, and may be thus uncomfortable. In addition, the absorbent core directly below the source of body exudate has a greater tendency to become saturated.

One solution to the potential problem of the hot and sticky feel of the apertured thermoplastic film is a sanitary absorbent article having a composite cover layer as described in International Patent Application Publication No. WO 93/09744. The composite cover layer described therein has a central zone extending longitudinally down the center of the article, and end zones extending laterally (transversely) from the central zone. The central zone comprises an apertured thermoplastic film, while the end zones comprise a non-woven material. The stated purpose of such a construction is to position the non-woven material in areas likely to come into contact with the skin of the wearer, while still retaining some of the benefit of having an apertured thermoplastic portion of the cover layer.

A cover layer of such construction suffers from two distinct problems. The first is that the regions of the cover layer which are near the transverse ends of the article also come into contact with the skin of the wearer, yet they still comprise a thermoplastic film. Thus, these portions may still feel hot and sticky to a wearer of the article. The second problem with such a construction is that the end zones (as described therein) still comprise a non-woven material in their marginal portions, thus any body exudate coming into contact therewith risks being wicked to the longitudinal edge of the article and staining the undergarments of the wearer. Moreover, it has been observed that generally, wearers of such articles would prefer to suffer a minor inconvenience in the form a slight hot and sticky feel rather than have the article fail to retain all of the body exudate impinging on it, and having their garments/undergarments soiled by such exudate.

There is therefore still a need in the art to provide a sanitary article having an improved cover layer construction. There is particularly a need to provide a sanitary absorbent article having reduced incidence of side leakage owing to lateral wicking along the cover layer, while reducing the hot and sticky feel associated with prior art articles having cover layers comprising apertured thermoplastic films.

SUMMARY OF THE INVENTION

It is thus an object of the present invention to pro vide a sanitary absorbent article having an improved cover layer construction.

It is another object of the present invention to provide a sanitary absorbent article having reduced incidence of side leakage owing to lateral wicking along the cover layer, while reducing, to some extent, the hot and sticky feel associated with prior art articles having cover layers comprising apertured thermoplastic films.

In accordance with the present invention, there has been provided a sanitary absorbent article adapted to be worn in a crotch portion of wearer's undergarment having a main body portion with two opposing longitudinal sides, two opposing transverse sides, an imaginary longitudinal centerline and an imaginary transverse centerline; the main body comprising:

(A) a fluid-pervious cover layer, the cover layer facing towards a wearer's body when the article is in use by a wearer;

(B) a fluid-impervious barrier layer, the barrier layer facing away from the wearer's body when the article is in use by the wearer;

(C) an absorbent system intermediate the cover layer and the barrier layer; the cover layer having:
   (1) an intermediate zone located in a centrial region of the main body and adapted for registration with a source of bodily exudate to be absorbed by the article when the article is in use by the wearer, the intermediate zone including marginal portions adjacent the respective longitudinal sides of the main body and extending towards the longitudinal centerline, the marginal portions comprising a material having a higher degree of vertical liquid migration than lateral liquid migration; and
   (2) a first terminal zone adjoining the intermediate zone and extending longitudinally away therefrom toward one of the transverse sides of the main body, the first terminal zone comprising a material having a higher degree of lateral liquid migration than vertical liquid migration.

The sanitary napkin of the present invention may optionally be provided with flexible flaps that project laterally outward from the longitudinal sides of the main body and which are adapted to be folded about the edges of the crotch portion of the undergarment. The longitudinal sides of the main body defines the interface or common boundary between the flaps and the main body and is not considered to form part of the flaps. Thus, with respect to embodiments of the present invention that do not possess flaps, the longitudinal sides of the main body also define the outer edges of the sanitary napkin.

In a specific nonlimiting example of implementation, each marginal portion has a minimum transverse dimension of not less than about 1.5 cm. The term "minimum transverse dimension" refers to a specific dimension of each marginal portion determinable as follows. A reference point on the sample of the sanitary absorbent article that is disposed beneath the source of bodily exudate, when worn, is located. A plane parallel to the transverse centerline and 2.0 centimeters forward from the reference point (a direction along the longitudinal centerline of the sanitary absorbent article) is located. Another plane parallel to the transverse centerline and 2.0 cm rearward from the reference point (a direction along the longitudinal centerline of the sanitary absorbent article) is also located. The smallest width of the marginal portion (the dimension measured along the transverse centerline of the sanitary absorbent article) occurring at any point between the two parallel planes defined above constitutes the "minimum transverse dimension" of the marginal portion. In a preferred embodiment, the minimum transverse dimension of each marginal portion is at least 2.0 cm.

Preferably, the cover layer further includes a second terminal zone adjoining the intermediate zone and extending longitudinally away therefrom toward the other of the transverse sides of the main body, the second terminal zone comprising a material having a higher degree of lateral liquid migration of bodily exudate than vertical liquid migration of bodily exudate.

It is preferred that the main body of the article be generally rectangular with rounded ends. When the article is of such a conformation, the first and second transverse sides are the shorter opposing sides and will generally have an arcuate shape. The first and second longitudinal sides are the longer opposing sides and may be substantially straight or arcuate, and are preferably inwardly arcuate to form a generally hour-glass or dog-bone shape.

The longitudinal centerline of the article is an imaginary line that extends longitudinally between the opposite transverse sides along an intermediate portion of the article which is substantially equidistant from the longitudinal sides thereof. It will thus bisect the article into two generally mirror image halves. As these articles are worn in the pudendal region, when the article is in use by a wearer, the longitudinal centerline thereof is generally parallel to, or most commonly, lies in, the sagital plane of the wearer. The transverse centerline is an imaginary line that extends transversely across the article, and is typically, but not always, equidistant from the transverse sides thereof. The transverse centerline is thus perpendicular to the longitudinal centerline. Where the article has flaps, the transverse centerline is generally the line perpendicular to the longitudinal centerline that bisects the flaps.

The article is of a laminate construction and in most cases will have at least three layers. The first of these layers is the cover layer. The cover layer has two major surfaces, the first is an external surface (i.e. a surface that does not face another component layer of the article), which, when the article is in use by a wearer, faces the wearer's body. The other surface is an internal surface (i.e. a surface that faces another component layer of the article), which faces the absorbent system below.

The cover layer is fluid-permeable, and thus will permit the body exudate to be absorbed by the article to pass through it into the layers below. The cover layer has an intermediate zone and two terminal zones. The intermediate zone is generally the zone of the article, which, when the article is correctly positioned with respect to the body of al wearer, is the initial contact point of the majority of the exudate to be absorbed by the article. Thus, when the article is a sanitary napkin, for example, the intermediate zone of the article will be located substantially in a central region of the article and is adapted to register with the vaginal opening of the wearer (the source of the exudate). The intermediate zone preferably has a longitudinal length, as measured along the longitudinal centerline of the article, of between about 2.5 and 12.5 cm and most preferably 7.5 cm.

In order to prevent bodily exudate to laterally wick across (in the plane of) the cover layer, the marginal portions thereof are constructed from a material that has a higher degree of vertical liquid migration than lateral liquid migration. The material of choice is selected such that when bodily exudate is deposited on the cover layer substantially no lateral liquid migration occurs (hereinafter this material is referred to as the "non-lateral liquid migration material" for ease of reference). Preferably this material is an apertured polymeric film, preferably apertured thermoplastic film having a three dimensional character. In the context of the present specification, the term "marginal portions" is used to indicate the regions of the intermediate zone of the cover layer adjacent the longitudinal sides of the main body and preferably starting at the longitudinal sides of the main body and extending inward towards the longitudinal centerline of the article. Preferably, the marginal portions comprising the non-lateral liquid migration material each comprise at least 15% of surface area of the total surface area of the intermediate zone. More preferably, they each comprise at least 20% of the total, still more preferably at least 25% of the total.

In accordance with one embodiment of the invention, the entire intermediate zone is a compound structure including a combination of a non-lateral liquid migration material and some other liquid pervious material wherein the marginal portions are constructed of the non-lateral liquid migration material to provide a barrier to lateral wicking. In accordance with this embodiment, the central area of the intermediate zone includes a non-woven fabric zone while the marginal portions of the intermediate zone are made of apertured film. In this form of construction, lateral liquid migration will occur in the non-woven fabric zone, but not in the marginal portions of the intermediate zone.

In order to increase the efficiency of the barrier (liquid migration resistance) effect of cover layers of this construction, it is preferred that the boundary between the two materials forming the intermediate zone lie interior (i.e. closer to the longitudinal centerline) than the edge of the absorbent system. In a specific example of implementation the distance (measured along the transverse centerline) separating the two boundaries is of about 5.0 cm while the width of the absorbent system is of about 6.6 cm.

In a most preferred embodiment of the invention, the entire intermediate zone is constructed of the non-lateral liquid migration material. In such a case, the non-lateral liquid migration material is still preferably an apertured thermoplastic film.

The terminal zones of the cover layer extend longitudinally from the intermediate zone to the transverse sides of the article. By "longitudinally" it is meant that the terminal zones extend in a direction generally parallel to the longitudinal centerline of the article. The terminal zones are in a large majority, and preferably in their entirety, constructed of a fibrous material, preferably a non-woven fibrous material, to be comfortable to the wearer of the article. The terminal zones do not need to be constructed from the same material.

The interface between portions of the cover layer being constructed of a non-lateral liquid migration material and portions constructed of a non-woven fibrous materials may take a variety of forms. It is most preferred that the portions constructed of non-lateral liquid migration material overlap those portions constructed of non-woven fibrous materials. In this manner, the non-woven fibrous material will laterally wick exudate underneath the non-lateral liquid migration materials, toward the absorbent system below.

The overlapping portions are sealed together by one of a variety of conventional means, e.g. by means of adhesives, heat-bonding, ultrasonic bonding, radio frequency sealing, mechanical crimping, and the like and combinations thereof. Adhesive sealing is preferred. To the greatest extent possible, the sealing method should leave a smooth surface on the body faceable surface of the cover layer so as avoid formation of irregularities that can irritate the user of the article.

It should be understood, however, that it is not required for the non-lateral liquid migration material to overlap the non-woven fibrous material. Executions where it is the non-woven fibrous material which overlaps the non-lateral liquid migration material, and those where the two materials abut one another, while not necessarily preferred, are all within the scope of the present invention. It should also be understood that the manner or position of the materials in which one interface is joined need not be identical with the manner or position of the materials in which another is joined.

Finally, for ease of manufacture, it is preferred that such interface be generally linear, and such lines be generally perpendicular to the longitudinal centerline (and thus parallel to the transverse centerline) or to the transverse centerline (and thus parallel to the longitudinal centerline), as the case may be. It should be understood, however, that non-linear interfaces are also within the scope of the present invention.

Preferably, the article will have a pair of flexible flaps, one flap extending laterally from each longitudinal side of the main body thereof. Such flaps are capable of being folded about the crotch portion of the undergarment of the wearer. The flaps serve several purposes, including stabilizing the article within the garment of the wearer, and protecting the garment from being soiled by body exudate not absorbed and/or retained by the article. Such flaps comprise extensions of the thermoplastic film material of the intermediate zone of said cover layer of said main boldy, and typically comprise extensions of the barrier layer as well, bonded thereto. This construction, i.e. the cover layer of the flap being formed from the non-lateral liquid migration material (preferably an apertured thermoplastic film), prevents lateral wicking along the surface of the flap.

The absorbent system is below the cover layer. The absorbent system may comprise a single layer or a composite layer combining multiple layers or additional structures, the primary purpose of all of which is to absorb and retain exudate. Many different absorbent systems are known in the art. The absorbent system has two major surfaces, both of which are internal surfaces, i.e. they both face other layers of the napkin. The first surface faces the cover layer, the second surface faces the barrier layer.

Underneath the absorbent system is the barrier layer. The primary purpose of the barrier layer is to prevent exudate absorbed within the napkin from egressing the napkin on the opposite from which it was absorbed. The barrier layer is thus impervious to liquid but could be made pervious to gases to provide breathability. The barrier layer has two major surfaces, an external surface that faces the undergarment of the wearer when the napkin is in use, and an internal surface that faces the absorbent system.

Preferably, the cover layer and the barrier layer are joined to one another to form a flange seal around the periphery of the article to thus form an envelope or casing that fully encloses the absorbent system to provide a structurally integral napkin. It is preferred that this envelope surround, and thus contain, the absorbent system within it. Conventional methods of adhering or uniting the various components of the article together, such as adhesive between the components, are all within the scope of the present invention.

Other objects and features of the invention will become apparent by reference to the following description and the drawings.

BRIEF DESCRIPTION OF THE DRAWINGS

A detailed description of preferred embodiments of the present invention is provided hereinbelow with reference to the following drawings, in which.

Figures 1, 2, 3:
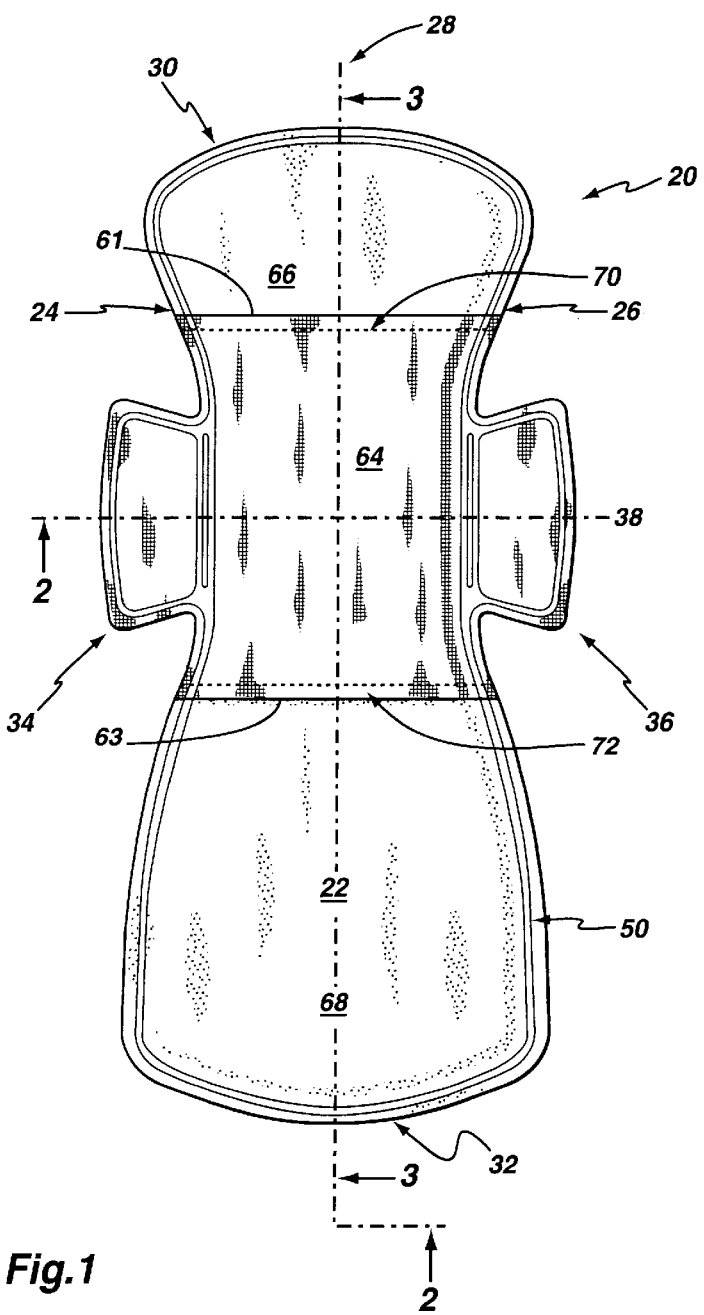
FIG. 1 is a top plan view of a first embodiment of the present invention in the form of a sanitary napkin.
FIG. 2 is a cross-sectional view of the sanitary napkin taken along the line 2—2 in FIG. 1.
FIG. 3 is a cross-sectional view of the sanitary napkin taken along the line 3—3 in FIG. 1.

In the drawings, preferred embodiments of the invention are illustrated by way of example. It is to be expressly understood that the description and drawings are only for purposes of illustration and as aid to understanding, and are not intended to be a definition of the limits of the invention.

DETAILED DESCRIPTION OF PREFERRED EMBODIMENTS

With reference to FIG. 1, there is shown a preferred embodiment of a sanitary absorbent article of the present invention, a disposable sanitary napkin 20. The napkin 20 comprises a main body 22. The main body 22 has two generally opposing longitudinal sides 24, 26, and an imaginary longitudinal centerline 28 running down the center of the napkin 20, generally equidistant from the longitudinal sides 24, 26. The longitudinal sides 24, 26 are concavely arcuate.

The main body 22 also has two generally opposing transverse sides 30, 32. The transverse sides are shown as convexly arcuate. Projecting laterally from each of the longitudinal sides 24, 26 of the main body 22 is a flap 34, 36 (respectively). The longitudinal sides 24, 26 form the interface or intermediate boundary between the main body 22 and the flaps 34, 36. The flaps 34, 36 are generally of the shape of an isosceles (i.e. bilaterally symmetrical) trapezoid, with the shorter of the two parallel sides thereof adjoining the longitudinal sides 24, 26 of the main body 22 of the napkin 20. An imaginary transverse centerline 38 runs across the napkin 20, perpendicular to the longitudinal centerline 28, and bisects the flaps 34, 36.

With reference to FIG. 2, the napkin 20 is a laminate structure and the main body 22 has a cover layer 40 which will face the body of a wearer when the napkin 20 is in use; a barrier layer 48, which will face the environment (i.e. away from the body of the wearer, and in almost all cases the wearer's undergarment) when the napkin 20 is in use; and an absorbent system 42 therebetween. The absorbent system 42 comprises a transfer layer 44 immediately underneath the cover layer 40 and an absorbent layer 46 between the transfer layer 44 and the barrier layer 48. The flaps 34, 36 comprise integral continuous extensions of the cover layer 40 and the barrier 48. Thus, the flaps 34, 36 are dual layer structures, the upper layer being a continuous extension of the cover layer 40 while the bottom layer is a continuous extension of the barrier layer 48. In the example of implementation of the invention depicted in FIG. 1, the upper layer of the flaps 34, 36 is made of the same material used for making the intermediate zone 64 of the cover layer 40, described in greater detail below. The flaps 34, 36 generally do not contain the absorbent system 42 therein. However, in an alternative embodiment, not shown in the drawings, the absorbent system may extend in the flaps or the flaps may be provided with separate absorbent layers. The cover layer 40 and the barrier layer 48 are sealed together along their peripheral edges (including the flaps 34, 36) to form a peripheral seal 50, containing the absorbent system 42.

Each of these layers will be described in further detail below.

Cover Layer

With reference to FIGS. 1 and 3, the cover layer 40 has an intermediate zone 64 extending across, generally parallel to and bisected by the transverse centerline 38. The flaps 34, 36 extend from the intermediate zone 64. Contiguous with, and extending longitudinally away from the intermediate zone 64, on either side of the transverse centerline 38, towards their respective transverse side 30, 32, are terminal zones 66, 68.

The intermediate zone 64 of the cover layer 40 is formed from an apertured thermoplastic film. Such films are common in the art. An example is the c-oextruded film described in U.S. Pat. No. 4,690,679, and marketed as RETICULON™ brand on sanitary napkins available from Johnson & Johnson Inc. of Montreal, Canada. Because of the high porosity of such films, they accomplish the function of quickly transferring body exudate to the inner layers (i.e. the absorbent system 42) of the napkin 20. Moreover, as such films are non-fibrous, they do not allow for lateral wicking of body exudate.

The terminal zones 66, 68 of the cover layer 40 are the portions of the cover layer 40 that extend from the longitudinal end portions 61, 63 of the intermediate zone 64 toward the transverse sides 30 and 32 of the sanitary napkin 20. In the specific non-limiting example of implementation depicted at FIG. 1, the terminal zones 66, 68 span the entire distance from the longitudinal end portions 61, 63 of the intermediate zone 64 to the transverse sides 30 and 32 of the sanitary napkin 20. Preferably, the terminal zones 66, 68 are formed of non-woven fibrous web material. Non-woven fibrous web materials are commonly known in the art. The terminal zones 66, 68 of the cover layer 40 may be composed of only one type of fiber, such as polyester, or may be composed of bicomponent or conjugate fibers having a low melting point component and a high melting point component. The fibers may be selected from a variety of natural and synthetic materials such as nylon, polyester, rayon (in combination with other fibers), cotton acrylic fiber and the like and combinations thereof. An example is the multi-denier cover layer described in the U.S. patent application Ser. No. 08/780,193 assigned to Johnson & Johnson. It will be evident to the person skilled in the art that a wide variety of other types of non-woven fabric materials can also be used.

Bicomponent fibers may be made up of a polyester core and a polyethylene sheath. The use of appropriate bicomponent materials results in a fusible non-woven fabric. Examples of such fusible fabrics are described in U.S. Pat. No. 4,555,430. Using a fusible fabric increases the ease with which the terminal zones 66, 68 of the cover layer 40 may be mounted to the adjacent transfer layer 44 and/or to the barrier layer 48.

The terminal zones 66, 68 of the cover layer 40 preferably have a relatively high degree of wettability, although the individual fibers comprising the zones may not be particularly hydrophilic. The terminal zone material should also contain a great number of relatively large pores. Preferably, the fibers which make up the terminal zones 66, 68 should not lose their physical properties when they are wetted, in other words they should not collapse or lose their resiliency when subjected to water or body fluid. They may be treated to allow fluid to pass through it readily. As with the intermediate zone 64, the terminal zones 66, 68 function to transfer the fluid quickly to the other layers of the absorbent structure. Thus, the terminal zones 66, 68 are preferably wettable, hydrophilic and porous. When composed of synthetic hydrophobic fibers such as polyolefin or bicomponent fibers, the zones may be treated with a surfactant to impart the desired degree of wettability.

The terminal zones 66, 68 are preferably manufactured from the same non-woven material, although this is not essential in the context of the present invention.

The material of the intermediate zone 64 and those of the terminal zones 66, 68 overlap one another (with that of the intermediate zone on top), and are joined together by seals 70, 72. The seals are created by bonding the overlapping portions together with adhesive, preferably, the adhesive under the commercial designation 34-5586 available from the National Starch & Chemical Corporation (Bridgewater, N.J., USA). The overlapping portions (and seals) are generally straight and perpendicular to the longitudinal centerline of the article 28.

Transfer Layer

Adjacent to the cover layer 40 on its inner side and bonded thereto is an optional fluid transfer layer 44, that may form part of the absorbent system 42. The transfer layer 44 provides the means of receiving body fluid from the cover layer 40 and holding it until the highly-dense absorbent layer 46 has an opportunity to absorb the fluid.

The transfer layer 44 is, preferably, more dense than and has a larger proportion of smaller pores than the cover layer 40. These attributes allow the transfer layer 44 to contain body fluid and hold it away from the outer side of the cover layer 40, thereby preventing the fluid from re-wetting the cover layer 40 and its surface. However, the transfer layer 44 is, preferably, not so dense as to prevent the passage of the fluid through the layer 44 into the absorbent layer 46 therebelow.

The transfer layer 44 may be composed of fibrous materials, such as wood pulp, polyester, rayon, flexible foam, or the like, or combinations thereof. The transfer layer 44 may also comprise thermoplastic fibers for stabilizing the layer and maintaining its structural integrity. The transfer layer 44 may be treated with surfactant on one or both sides in order to increase its wettability, although generally the transfer layer 44 is relatively hydrophilic and may not require treatment. The transfer layer 44 is preferably bonded on both sides to the adjacent layers, i.e. the cover layer 40 and the absorbent layer 46. An example is the material sold by Merfin in the United-States under the commercial designation VICELL 6002.

Absorbent Layer

Immediately adjacent to and bonded to the transfer layer 44 is the absorbent layer 46 that forms part of the absorbent system 42. The absorbent system 42 may comprise only the absorbent layer 46 or it may comprise a plurality of layers, such as the absorbent layer 46 in combination with the transfer layer 44 or any other additional layer. This is to say that the transfer layer 44 is not an essential component of the present invention.

The absorbent layer 46 is preferably a highly dense layer having a fine porosity. It has a large liquid holding capacity and it is extremely retentive. In a specific nonlimiting example of implementation of the present invention, the absorbent layer 46 is composed of compressed sphagnum moss material. More specifically, the sphagnum moss is formed as a board by air or wet laying and calendering to obtain a relatively thin, i.e. from about 0.025 to 0.25 cm thick, relatively dense, i.e. from about 0.2 to 1.0 g/cm$^3$ sheet like structure. The structure may include a layer of Kraft tissue laminated on one or both surfaces of the sphagnum moss layer. Preferably, a fibrous component is admixed with the sphagnum moss material. The fibrous component is suitably a natural or synthetic textile fiber such as rayon, polyester, nylon, acrylic or the like, having a length of from about 0.625 to 3.75 cm inches and a denier of from about 1.0 to 5. The fibrous component may be present in an amount from about 2 to 20% by weight, most preferably from 4 to 8%. The absorbent layer 46 may also comprise other components such as wood pulp, synthetic wood pulp, thermomechanical pulp, mechanically ground pulp, polymers, surfactants, superabsorbents and the like.

In an alternative embodiment the absorbent layer 46 comprises a pulp fluff material and may optionally include other absorbent materials or non-absorbent materials which aid in stabilizing the absorbent structure such as conjugate fibers, fusible fibers, binders, sphagnum peat moss particles, superabsorbents, and the like and combinations thereof; and may optionally include other absorbent materials or non-absorbent materials which aid in stabilizing the absorbent structure such as conjugate fibers, fusible fibers, binders, sphagnum peat moss particles, superabsorbents, and the like and combinations thereof.

The absorbent system 42 has two longitudinal sides 73 (only one is shown in the Figures in FIG. 2) which are each generally parallel to the longitudinal sides 24, 26 of the main body 22 of the napkin 20. Where the absorbent system 42 comprises a composite laminate structure (as opposed to a single layer), the longitudinal sides 73 thereof should be considered to be the longitudinal sides of the component thereof having the largest width, as measured along the transverse centerline of the article.

The longitudinal sides 73 of the absorbent system 42 are interior to the longitudinal sides 24, 26 of the main body 22. I.e. the distance from the longitudinal centerline 28 to the longitudinal side 73 of the absorbent layer 46 is less the distance from the longitudinal centerline 28 to the corresponding point on the longitudinal side 24 of the main body 22 of the napkin 20.

Barrier Layer

Underlying the absorbent system 42 is a barrier layer 48 comprising liquid-impervious film material so as to prevent liquid that is entrapped in the absorbent layer 46 from egressing the sanitary napkin 20 and staining the wearer's undergarment. Most preferably, the barrier layer 48 is made of polymeric film, such as polyethylene or polyethylenelethylvinyl acetate (EVA), which are both inexpensive and readily available. The polymeric film is capable of fully blocking the passage of liquid or gas that may emanate from the absorbent system 42. In a variant, breathable films may be used that allow passage of gases while blocking liquid. A suitable example is a combination polyethylene/ethylvinyl acetate (EVA) film sold by the Edison Plastics Company in the United-States under the commercial designation XP-1167B.

Adhesives

Figure 4:
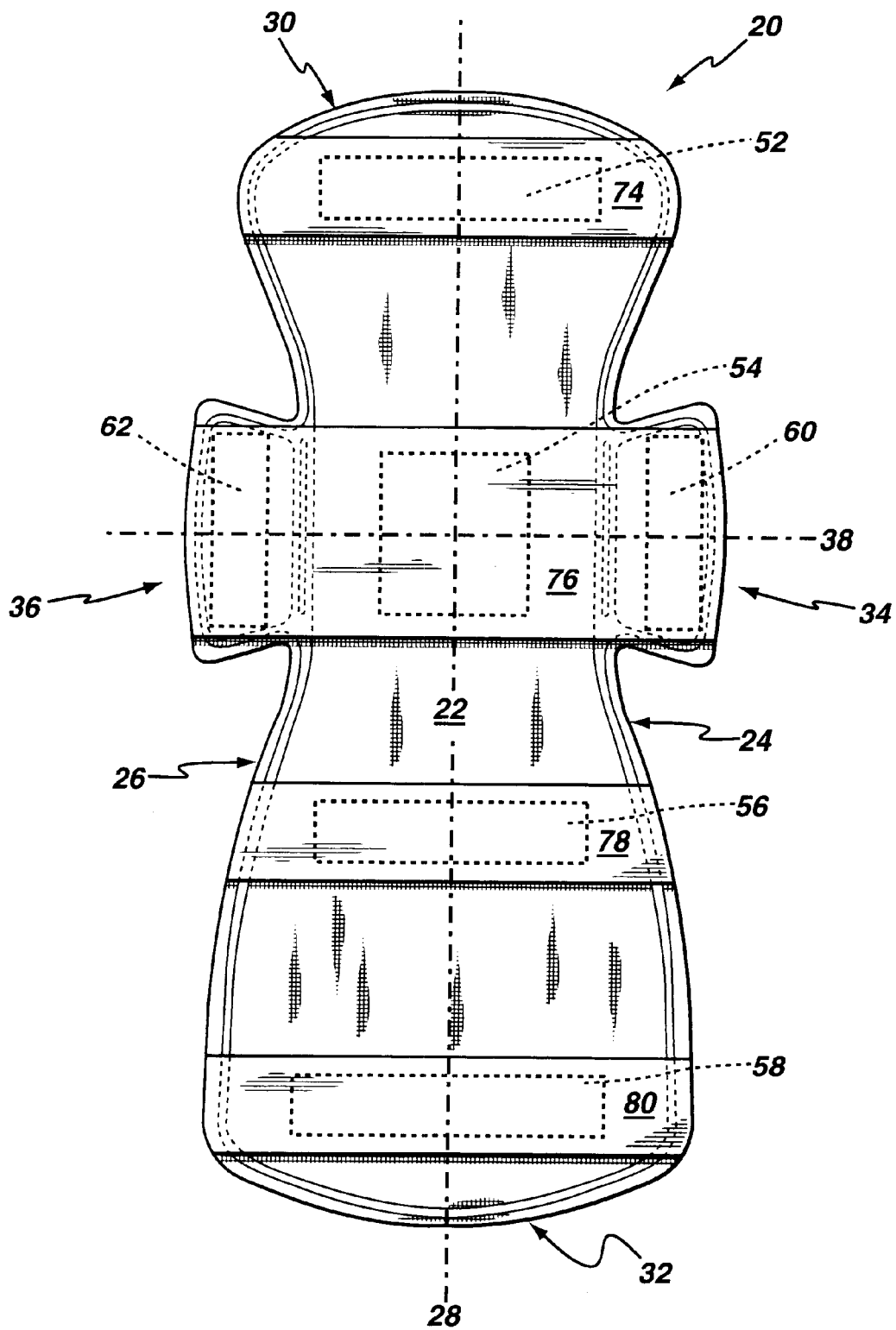
FIG. 4 is a bottom plan view of a sanitary napkin of the present invention.

Referring to FIG. 4, in order to secure the napkin 20 to the undergarment of a wearer, the barrier layer 48 is provided with a plurality of areas of standard adhesive material 52, 54, 58, 60, 62 ("adhesives") on the environmental (i.e. undergarment) facing surface thereof. Specifically four of such adhesives are located on the main body 22 of the napkin 20; one 52 close to one 30 of the transverse sides; another 58 close to the other 32 of the transverse sides; a third 54 in the intermediate region of the napkin 20 in between the flaps 34, 36; and a fourth 56 between the second 58 and that 54 in the intermediate region. Additionally, there is an adhesive 60, 62 located on each of the flaps 34, 36 (respectively). Standard release papers 74, 78, 80 individually cover three of the adhesives 52, 56, 58. A single standard release paper 76 covers the adhesive 54 in the intermediate region of the main body 22 and those 60, 62 on the flaps 34 36. A suitable adhesive is the composition designated HL-1491 XZP commercially available from H. B. Fuller Canada, Toronto, Ontario, Canada. The release papers are of conventional construction (silicone coated wet-laid Kraft wood pulp) and suitable papers are available from Tekkote Corp ration (Leonia, N.J., USA), and bear the designation FRASER 30#/61629.

Sanitary napkin 20 is fabricated in accordance with conventional techniques. Specifically, a laminate structure, sometimes referred to in the art as a web, is created. This laminate structure comprises an expanse of the materials from which the napkin will be created. I.e., the laminate structure comprises an expanse of cover layer materials, underneath transfer layer material, underneath absorbent layer material, and finally underneath an expanse of barrier layer material. Some of the materials are not necessarily continuous within the laminate structure, and where such is the case, they are positioned precisely, one with respect to another, in the relationship they will occupy in the final products. The cover layer material and the barrier layer material are then bonded together by applying pressure in the appropriate positions, and what will become the peripheral seal is created. (The seal may also be made by means of heat-bonding, ultrasonic bonding, radio frequency sealing, mechanical crimping, and the like and combinations thereof.) The sealed structure is then severed by conventional means (e.g. die-cutting, fluid-jet cutting, or by laser) from the web to create a discrete article.

The adhesive material is then applied to the barrier layer in the appropriate positions, and release paper is applied to cover the adhesive. Alternatively, the adhesive, or the adhesive and the release paper may be applied to the web before the individual articles are severed therefrom. In use, the release paper is removed, and the napkin is positioned within the undergarment of a wearer. Once used, the napkin is disposed of.

Alternative Embodiments

Figure 5:
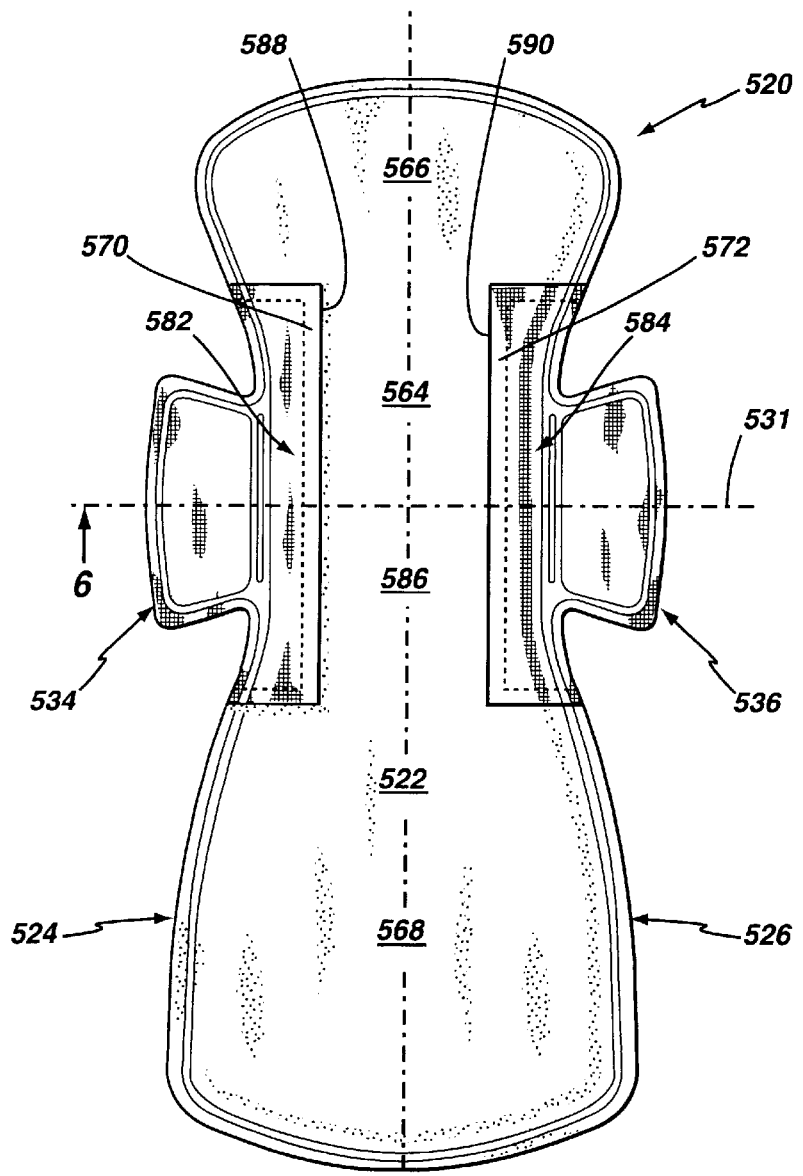
FIG. 5 is a top plan view of a second embodiment of the present invention in the form of a sanitary napkin.
Figure 6:
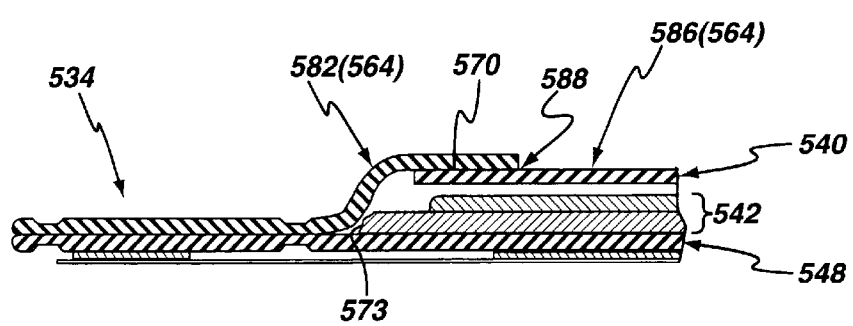
FIG. 6 is a cross-sectional view of the sanitary napkin taken along the line 6—6 in FIG. 5.

Referring to FIGS. 5 and 6, there is a shown a sanitary napkin 520 being a second embodiment of the present invention. The napkin 520 is similar in construction (and fabrication) to the previous embodiment described hereinabove, with the exception of the cover layer 540.

The cover layer 540 has an intermediate zone 564 and two terminal zones 566, 568. The intermediate zone 564 has marginal portions 582, 584 and an interior portion 586. The marginal portions 582, 584 of the intermediate zone 564 comprise an apertured thermoplastic film (as described hereinabove). The interior portion 586 of the intermediate zone 564 comprises a non-woven fibrous material (as described hereinabove). The material of the interior portion 586 is continuous (and integral) with that of the terminal zones 566, 568. It should be understood, however, that executions where the interior portion 586 is a different material than that of either or both of the terminal zones 566, 568 are also within the scope of the present invention.

The marginal portion 582, 584 material overlaps the material of the interior portion 586 of the intermediate zone 564 and that of the terminal zones 566, 586. The various materials are sealed together at seals 570 and 572 as described hereinabove. As with the previous embodiment it should be understood that executions where the marginal portion material underlies or abuts that of the interior portion and the transverse zones (or any combination thereof) are also within the scope of the present invention.

The edge 588, 590 of each marginal portion 582, 584 (respectively) lies interior to the corresponding edge 573 (i.e. the edge on the same side of the longitudinal centerline 528) of the absorbent system 542. I.e. the distance from the longitudinal centerline 528 to the edge 588 of the marginal portion 582 is less than the distance from the longitudinal centerline 528 to the edge 573 of the absorbent system 542. In a specific non-limiting example of implementation the distance between the edge 588 and 590 measured along to the transverse centerline 531 is of about 5.0 cm while the transverse dimension of the absorbent system 542 is of about 6.6 cm. It should be noted that the transverse dimension of the absorbent system 542, in the case where the absorbent system 542 is made of a plurality of layers is the transverse dimension of the layer that has the largest transverse dimension of the group.

In a specific nonlimiting example of implementation, each marginal portion 582, 584 has a minimum transverse dimension of not less than about 1.5 cm. The term "minimum transverse dimension" refers to a specific dimension of each marginal portion 582, 584 of the sanitary napkin 520 determinable as follows. A reference point on the sanitary napkin that is disposed beneath the source of bodily exudate, that in this case is the vaginal orifice, is located. A plane parallel to the transverse centerline 531 and 2.0 centimeters forward from the reference point (a direction along the longitudinal centerline 528 of the sanitary napkin 520) is located. Another plane parallel to the transverse centerline 531 and 2.0 cm rearward from the reference point (a direction along the longitudinal centerline 528 of the sanitary napkin 520) is also located. The smallest width of the marginal portion 582, 584 (the dimension measured along the transverse centerline of the sanitary napkin 520) occurring at any point between the two parallel planes defined above constitutes the "minimum transverse dimension" of the marginal portion. In the example of implementation depicted in FIG. 5, the endpoints of the width of each marginal portion 582, 584 are the longitudinal side and the interior edge 588, 590. In the area of the flap 534, 536 the measurement is taken from the line of juncture where the flap 534, 536 connects to the longitudinal side of the sanitary napkin 520.

In a possible variant, the minimum transverse dimension of each marginal portion is of at least 2.0 cm.

Flaps 534, 536 project from the longitudinal sides 524, 526 (respectively) of the main body 522 of the napkin 520. The flaps 534, 536 comprise integral extensions of the material of the marginal portions 582, 584 (respectively) of the cover layer 540 and of the material of the barrier layer 548.

In all other respects, the construction of the present embodiment, its manufacture and use are similar to that described hereinabove in detail in relation to the previously described embodiment.

Figure 7:
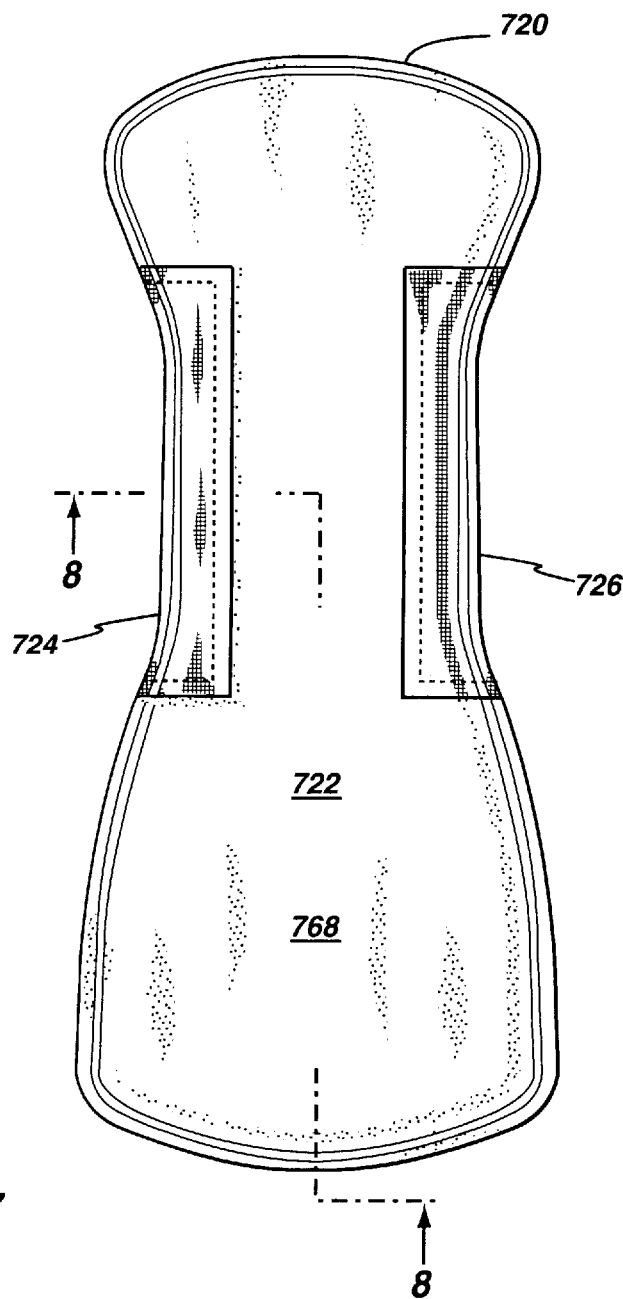
FIG. 7 is a top plan view of a third embodiment of the present invention in the form of a sanitary napkin.
Figure 8:
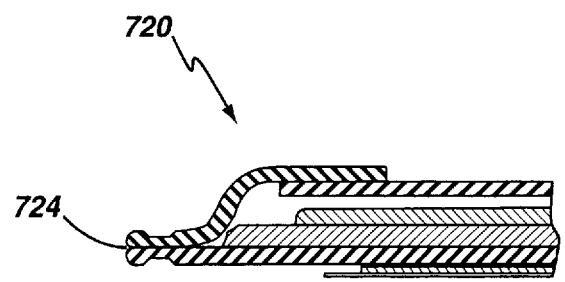
FIG. 8 is a cross-sectional view of the sanitary napkin taken along the line 8—8 in FIG. 7.

Referring to FIGS. 7 and 8, there is a shown a sanitary napkin 720 being a third embodiment of the present invention. The napkin 720 is similar in construction to the previous embodiment described hereinabove, with the exception of that no flaps extend from the longitudinal sides 724, 726 of the main body 722 thereof. In this embodiment, the longitudinal sides 724, 726 form part of the outer edges of the main body 722.

Figure 9:
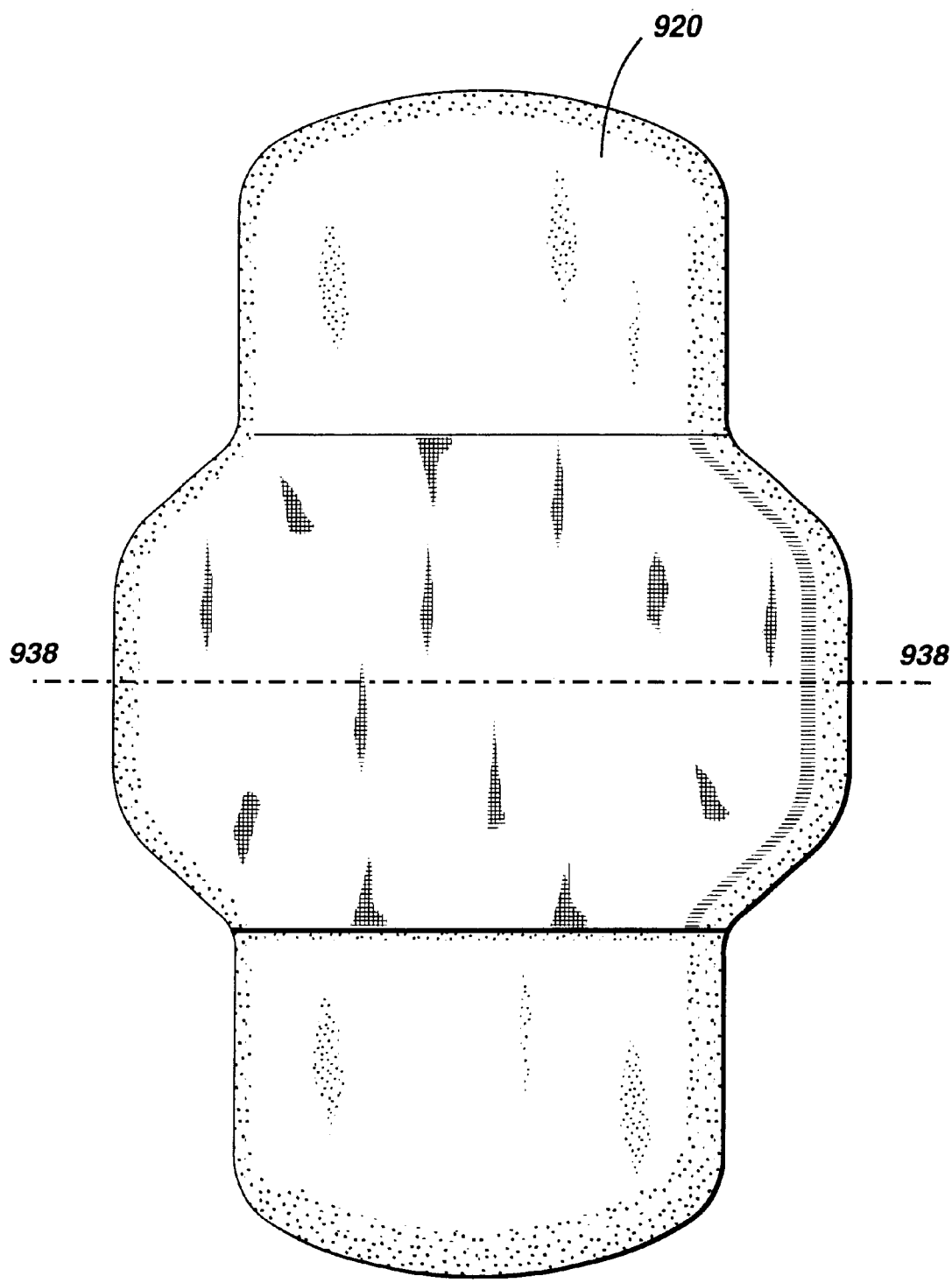
FIG. 9 is a top plan view of a sanitary napkin according to a third embodiment of the present invention.

Referring to FIG. 9, there is a shown a sanitary napkin 920 being a fourth embodiment of the present invention. The napkin 920 is similar in construction to the first embodiment previously described hereinabove, with exception that it has the shape of a napkin typically used for daytime use. It is symmetric about its transverse axis 938.

I claim:

1. A sanitary absorbent article adapted to be worn in a crotch portion of a wearer's undergarment having a main body, said main body having two opposing longitudinal sides, two opposing transverse sides, an imaginary longitudinal centerline and an imaginary transverse centerline; said main body comprising:

(A) a fluid-pervious cover layer, said cover layer facing towards a wearer's body when the article is in use by a wearer;

(B) a fluid-impervious barrier layer, said barrier layer facing away from the wearer's body when the article is in use by the wearer;

(C) an absorbent system intermediate said cover layer and said barrier layer; said cover layer having:
  (1) an intermediate zone located in a central region of said main body and adapted for registration with a source of bodily exudate to be absorbed by the article when the article is in use by the wearer, said intermediate zone including marginal portions extending from respective longitudinal sides of said main body towards the longitudinal centerline, said marginal portions being substantially vertically aligned with said absorbent system comprising a material having a higher degree of vertical liquid migration than lateral liquid migration; and
  (2) a first terminal zone adjoining said intermediate zone and extending longitudinally away therefrom toward one of the transverse sides of said main body, said first terminal zone comprising a material having a higher degree of lateral liquid migration than vertical liquid migration.

2. A sanitary article as recited in claim 1, wherein each marginal portion has a minimum transverse dimension not less than about 1.5 cm.

3. A sanitary article as recited in claim 2, wherein each marginal portion has a minimum transverse dimension not less than about 2.0 cm.

4. A sanitary article as recited in claim 3, wherein said material having a higher degree of vertical liquid migration than lateral liquid migration comprises polymeric film.

5. A sanitary article as recited in claim 4, wherein said polymeric film is apertured.

6. A sanitary absorbent article as recited in claim 5, further comprising flaps extending laterally from the longitudinal sides of said main body, said flaps capable of being folded about a crotch portion of an undergarment of the wearer, said flaps comprising extensions of the apertured polymeric film of the intermediate zone of the cover layer of said main body.

7. A sanitary article as recited in claim 2, wherein said material having a higher degree of vertical liquid migration than lateral liquid migration extends continuously from one longitudinal side of said sanitary article to an opposite longitudinal side thereof.

8. A sanitary article as recited in claim 2, wherein said material having a higher degree of lateral liquid migration than vertical liquid migration comprises fibrous material.

9. A sanitary absorbent article as recited in claim 2, wherein said cover layer further includes a second terminal zone adjoining said intermediate zone and extending longitudinally away therefrom toward the other of the transverse sides of said main body, the first and the second terminal zones comprising fibrous material having a higher degree of lateral liquid migration than vertical liquid migration.

10. A sanitary absorbent article as recited in claim 9, wherein the fibrous material of the terminal zones is a non-woven fibrous material.

11. A sanitary absorbent article as recited in claim 1, wherein the intermediate zone of said cover layer is characterized by a surface area and the marginal portions of said intermediate zone together comprise at least 10% of the surface area of said intermediate zone.

12. A sanitary absorbent article as recited in claim 11, wherein the marginal portions of said intermediate zone together comprise at least 25% of the surface area of said intermediate zone.

13. A sanitary absorbent article as recited in claim 11, wherein the marginal portions of said intermediate zone together comprise at least 50% of the surface area of said intermediate zone.

14. A sanitary absorbent article as recited in claim 11, wherein the marginal portions of said intermediate zone together comprise at least 75% of the surface area of said intermediate zone.

15. A sanitary absorbent article as recited in claim 11, wherein the entire intermediate zone of said cover layer is formed of the material having a higher degree of vertical liquid migration than lateral liquid migration.

16. A sanitary absorbent article as recited in claim 1, wherein the intermediate zone of the cover layer is between about 2.5 cm and about 12.5 cm in longitudinal length.

17. A sanitary absorbent article as recited in claim 16, wherein the intermediate zone of the cover layer is about 7.5 cm in longitudinal length.

18. A sanitary absorbent article as recited in claim 1, wherein the article is a sanitary napkin.

19. A sanitary absorbent article as recited in claim 1, wherein the article is a pantiliner.

20. A sanitary absorbent article as recited in claim 1, wherein the article is an incontinence pad.

* * * * *